US006106576A

United States Patent [19]

Fromson

[11] Patent Number: 6,106,576

[45] **Date of Patent: *Aug. 22, 2000**

[54] ADJUSTABLE MASSAGE BED ASSEMBLY WITH HANDHELD CONTROL UNIT HAVING AUTOMATIC STOP SAFETY FEATURE

[75] Inventor: Leonard E. Fromson, La Mirada, Calif.

[73] Assignee: Maxwell Products, Inc., Cerritos, Calif.

[ * ] Notice: This patent is subject to a terminal disclaimer.

[21] Appl. No.: 08/649,261

[22] Filed: May 17, 1996

Related U.S. Application Data

[62] Division of application No. 08/277,511, Jul. 19, 1994.

[51] Int. Cl.[7] .......................... C12N 5/00

[52] U.S. Cl. .......................... 818/16

[58] Field of Search .......................... 318/16, 563, 560; 5/915, 616, 618

[56] References Cited

U.S. PATENT DOCUMENTS

| | | |
|---|---|---|
| D. 187,923 | 5/1960 | Przybylowicz et al. . |
| D. 266,501 | 10/1982 | Stefanik . |
| D. 266,758 | 11/1982 | Johannse et al. . |
| D. 293,669 | 1/1988 | Ogilvie . |
| D. 342,259 | 12/1993 | Darlee et al. . |
| 3,137,773 | 6/1964 | Black . |
| 3,644,946 | 2/1972 | Swatt . |
| 3,711,664 | 1/1973 | Benoit et al. . |
| 3,716,876 | 2/1973 | Petzon et al. . |
| 3,781,927 | 1/1974 | Zakaras . |
| 3,865,430 | 2/1975 | Tanus . |
| 3,913,153 | 10/1975 | Adams et al. . |
| 3,923,300 | 12/1975 | Tanus . |
| 3,932,903 | 1/1976 | Adams et al. . |
| 3,972,081 | 8/1976 | Stern et al. . |
| 4,014,344 | 3/1977 | Gutierrez . |
| 4,044,286 | 8/1977 | Adams et al. . |

(List continued on next page.)

FOREIGN PATENT DOCUMENTS

| | | |
|---|---|---|
| 0092197 | 10/1983 | European Pat. Off. . |
| 0178951 | 4/1986 | European Pat. Off. . |
| 0220708 | 5/1987 | European Pat. Off. . |
| 0261830 | 3/1988 | European Pat. Off. . |
| 0302579 | 2/1989 | European Pat. Off. . |
| 0316643 | 5/1989 | European Pat. Off. . |
| 0341358 | 11/1989 | European Pat. Off. . |
| 0341570 | 11/1989 | European Pat. Off. . |
| 0348726 | 1/1990 | European Pat. Off. . |
| 0373912 | 6/1990 | European Pat. Off. . |
| 0453363 | 10/1991 | European Pat. Off. . |
| 0455852 | 11/1991 | European Pat. Off. . |
| 0488552 | 6/1992 | European Pat. Off. . |
| 0505312 | 9/1992 | European Pat. Off. . |
| 0505847 | 9/1992 | European Pat. Off. . |
| 2630334 | 1/1978 | Germany . |
| 3119876 | 12/1982 | Germany . |
| 3109166 | 1/1983 | Germany . |
| 54-045472 | 4/1979 | Japan . |
| 54-045473 | 4/1979 | Japan . |
| 4322611 | 11/1992 | Japan . |
| 5095978 | 4/1993 | Japan . |
| 8902202 | 3/1991 | Netherlands . |
| 1404038 | 8/1975 | United Kingdom . |
| 2210554 | 6/1989 | United Kingdom . |
| WO9006739 | 6/1990 | WIPO . |

*Primary Examiner*—Karen Masih
*Attorney, Agent, or Firm*—Blakely, Sokoloff Taylor & Zafman LLP

[57] ABSTRACT

An adjustable massage bed assembly including a head motor for controllably raising and lowering a head section of a mattress, a foot motor for controllably raising and lowering a foot section of the mattress, and a vibratory motor for imparting a massaging action to the mattress. A handheld control unit has first and second mechanisms for controlling operations of the head and foot motors, and a third mechanism for controlling an operation of the vibratory motor. The third mechanism when actuated also automatically stops any ongoing operation of the head and foot motors as a safety feature.

14 Claims, 5 Drawing Sheets

U.S. PATENT DOCUMENTS 4,062,075 12/1977 Stern et al. .
4,211,998 7/1980 Junginger et al. .
4,218,681 8/1980 Hormann .
4,231,019 10/1980 Junginger et al. .
4,232,901 11/1980 Harrington et al. .
4,294,048 10/1981 Sutter .
4,435,862 3/1984 King et al. .
4,680,790 7/1987 Packard et al. .
4,712,105 12/1987 Kohler .
4,754,255 6/1988 Sanders et al. .
4,769,584 9/1988 Irigoyen et al. .
4,787,104 11/1988 Grantham .
4,798,197 1/1989 Nippoldt et al. .
4,825,200 4/1989 Evans et al. .
4,850,040 7/1989 Teich et al. .
4,878,055 10/1989 Kashara .
4,999,622 3/1991 Amano et al. .
5,044,029 9/1991 Vrzalik .
5,053,636 10/1991 Zelina .
5,058,871 10/1991 Cogin et al. .
5,062,167 11/1991 Thomas et al. .
5,063,623 11/1991 Bathrick et al. .
5,063,624 11/1991 Smith et al. .
5,072,463 12/1991 Willis .
5,073,999 12/1991 Thomas et al. .
5,098,089 3/1992 Harrington et al. .
5,107,554 4/1992 Garakani .
5,235,258 8/1993 Schuerch .
5,239,300 8/1993 Berger et al. .
5,388,691 2/1995 White .................................... 206/305
5,577,280 11/1996 Elliott ........................................ 5/618
5,600,214 2/1997 Fromson .

FIG. 6
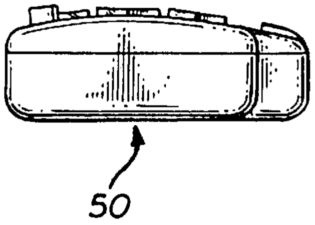
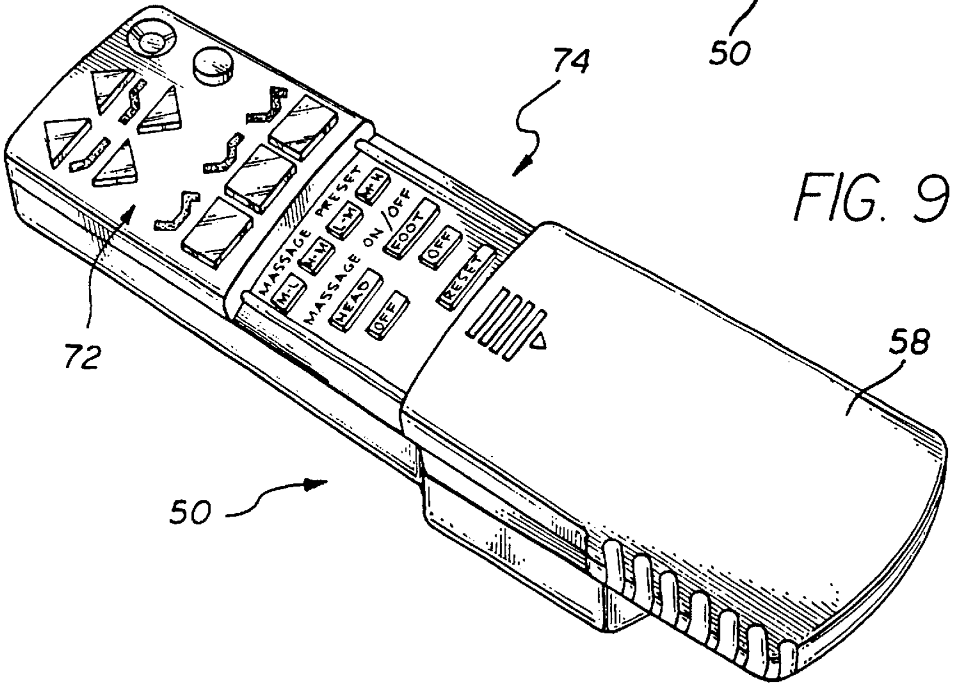
FIG. 9
FIG. 7
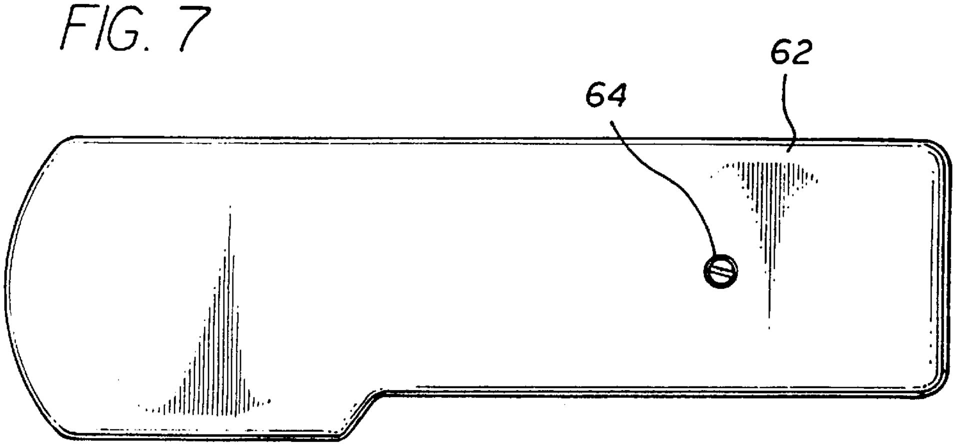
FIG. 8
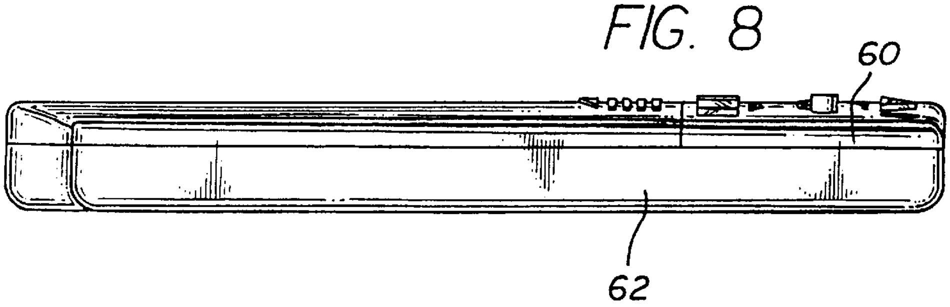

ADJUSTABLE MASSAGE BED ASSEMBLY WITH HANDHELD CONTROL UNIT HAVING AUTOMATIC STOP SAFETY FEATURE

CROSS-REFERENCE TO RELATED APPLICATION

This is a divisional of copending application Ser. No. 08/277,511 filed on Jul. 19, 1994 pending.

BACKGROUND OF THE INVENTION

1. Field of the Invention

The present invention relates to an articulated bed assembly with a simplified remote control and, more particularly, pertains to an articulated bed assembly with a simplified remote control unit including several groups of buttons only one of which is accessible to the user when a face cover of the remote control unit is slid into a closed position.

2. Description of the Related Art

An articulated bed includes one or several mechanisms which allow different portions of the bed to be tilted or otherwise positionally adjusted. The comfort of individuals who are "bedridden" may be enhanced by providing an articulated bed that is easily adjusted. Although various mechanisms for adjusting the configuration of a bed are known, the art is still without an articulated bed assembly which includes, and is remotely controlled by, a simplified remote control unit.

Accordingly, an object of the present invention is to provide an articulated bed assembly with a simplified remote control unit.

Another object is to provide an articulated bed assembly with a simplified remote control unit that includes several groups of buttons some of which may be concealed from the user's view by a slidable face cover.

Still another object of the present invention is to provide an articulated bed assembly with a simplified remote control unit which additionally allows the user to select from a number of preset bed positions by pressing a single button which is designated by an icon identifying the desired preset bed position.

Yet another object of the present invention is to provide an articulated bed assembly with a simplified remote control unit which allows a stored massage mode to be recalled with a single button.

Another object of the present invention is to provide an articulated bed assembly with a simplified remote control unit that further includes head and foot massage motors which operate at preset massage modes and which may be manually adjusted to operate at low, medium and high frequencies via the remote control unit.

An additional object of the present invention is to provide an articulated bed assembly with a simplified remote control unit wherein the operating frequencies of the head and foot massage motors are selected to provide a beat frequency vibration effect between head and foot portions of the bed.

SUMMARY OF THE INVENTION

In accordance with a specific illustrative embodiment of the present invention, an articulated bed assembly with a simplified remote control unit includes a head elevation motor for raising or lowering a head position of the bed in response to a head elevation signal, and a foot elevation motor for raising or lowering a foot portion of the bed in response to a foot elevation signal. The bed assembly further includes a head massage motor for vibrating the head portion of the bed in response to a head massage signal, and a foot massage motor for vibrating the foot portion of the bed in response to a foot massage signal. The bed assembly also includes a simplified remote control unit with a plurality of user activated mechanisms (such as buttons), an encoder and a transmitter. The user activated mechanisms provide user input signals to the encoder when a user activates the mechanisms. The various user activated mechanisms provide a raised head portion signal, a lower head portion signal, a raised foot portion signal, a lower foot portion signal, a bed position preset signal, a stored massage signal, a head massage motor speed signal, a foot massage motor speed signal, and a massage motors preset signal as the user input signals. The encoder encodes the user input signals to provide an encoded signal which is transmitted as a modulated encoded signal by the transmitter. The bed assembly additionally includes a bed controller unit with a receiver, a decoder, and logic circuitry. The modulated encoded signal is received and demodulated by the receiver to provide the encoded signal to the decoder which decodes the encoded signal to provide the user input signals. The logic circuitry generates the head elevation signal, the foot elevation signal, the head massage signal, and the foot massage signal from the user input signals.

In a further aspect of the present invention, the simplified remote control unit serves as an improvement to an articulated bed assembly and includes a plurality of buttons as the user activated mechanisms. The plurality of buttons includes a first and second group of buttons. Such a simplified remote control unit additionally includes a slidable face cover which conceals the second group of buttons when the face cover is slid into a closed position.

In other words, disclosed herein is an articulated bed assembly with a simplified remote control unit, head and foot elevation motors, head and foot massage motors and a bed controller unit. The simplified remote control unit includes an encoder and a transmitter for providing user input signals to the bed controller unit. The simplified remote control unit also includes groups with some of the buttons which are proximately arranged and geometrically shaped according to function with some of the buttons being concealable behind a face cover of the remote control unit. The bed controller unit includes a receiver, a decoder and logic circuitry for retrieving the user input signals and generating command signals to the head and foot elevation motors and the head and foot massage motors.

DESCRIPTION OF THE DRAWINGS

Other objects, features and advantages of the invention will become readily apparent upon reference to the following detailed description when considered in conjunction with the accompanying drawings, in which like reference numerals designate like parts throughout the figures thereof, and wherein

FIG. 6 is a top view of the simplified remote control unit;

FIG. 7 is a rear view of the simplified remote control unit;

FIG. 8 is a right side view of the simplified remote control unit;

FIG. 9 is a perspective view of the simplified remote control unit showing a slidable face cover of the unit in an opened position;

DETAILED DESCRIPTION OF THE PREFERRED EMBODIMENTS

Figure 1:
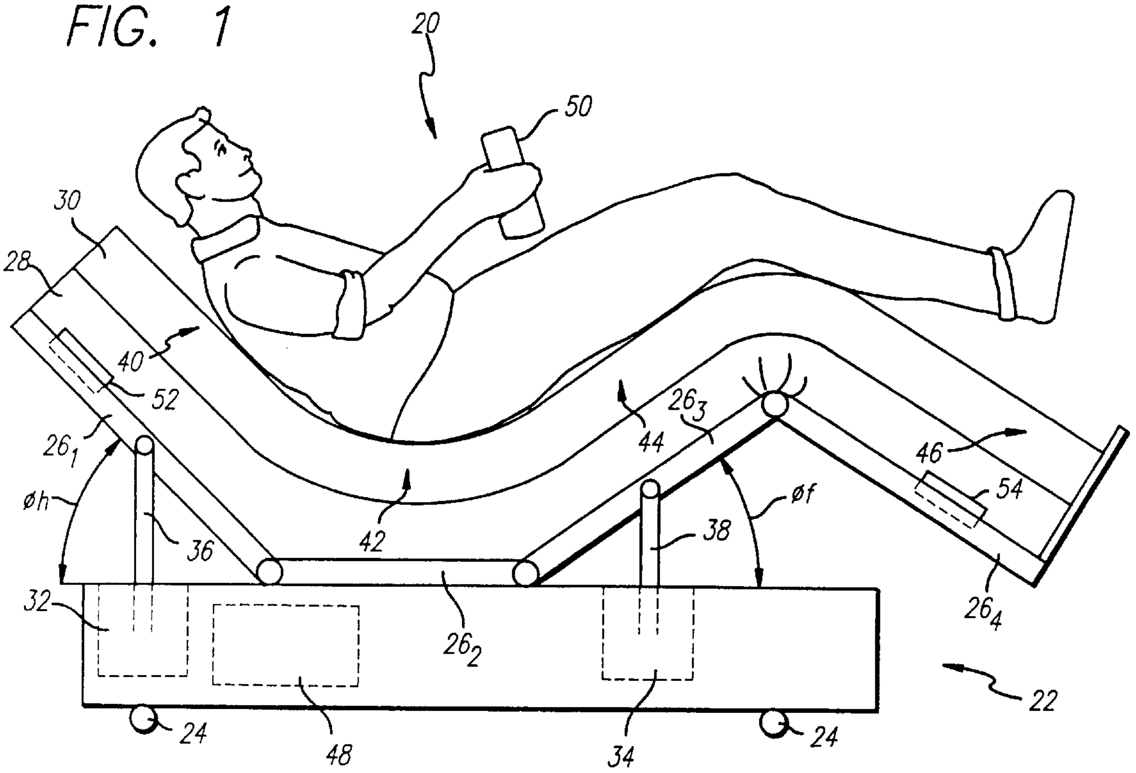
FIG. 1 is side view of the articulated bed assembly of the present invention.

FIG. 1 shows an articulated bed assembly 20 of the present invention which includes a base 22 which may be, but is not necessarily, supported by wheels or casters 24. The bed assembly 20 includes articulated support plates $26_1$, $26_2$, $26_3$, $26_4$ which supports a cloth covered foam layer 28 and a mattress 30.

A head elevation motor 32 and a foot elevation motor 34 are assembled within and/or attached to the base 22. The elevation motors 32, 34 are conventional and respectively drive linear actuators 36, 38.

As is shown in FIG. 1, the bed assembly 20 may be approximately partitioned into a head portion 40, a midriff portion 42, a thigh portion 44 and a foot portion 46 along a length of the mattress 30. Below the head portion 40, the support plate $26_1$ is mechanically connected to the linear actuator 36 and is raised or lowered in elevation by the head elevation motor 32. Similarly, the support plate $26_3$ which is positioned beneath the thigh portion 44 is mechanically connected to the linear actuator 38 and is raised or lowered in elevation by the foot elevation motor 34. The elevation motors 32, 34 are both electrically connected to and driven by a bed controller unit 48 which is preferably assembled within the base 22. The bed assembly 20 also includes a simplified remote control unit 50 for transmitting a modulated encoded signal to the bed controller unit 48. Generally, a user is able to manipulate the bed assembly 20 into one of several predetermined bed positions, via the bed controller unit 48, by pressing an appropriate button on the remote control unit 50. The bed assembly 20 additionally includes a head massage motor 52 and a foot massage motor 54 which are respectively attached to the support plates $26_1$, $26_4$. The massage motors 52, 54 are controlled by and electrically connected to the bed controller unit 48 and vibrate the foam layer 28 and the mattress 30 when appropriately driven. As with the elevation motors 32, 34, the massage motors 52, 54 are controlled, via the bed controller unit 48, by a user who presses buttons on the remote control unit 50 which are dedicated to controlling the massage motors.

Figure 2:
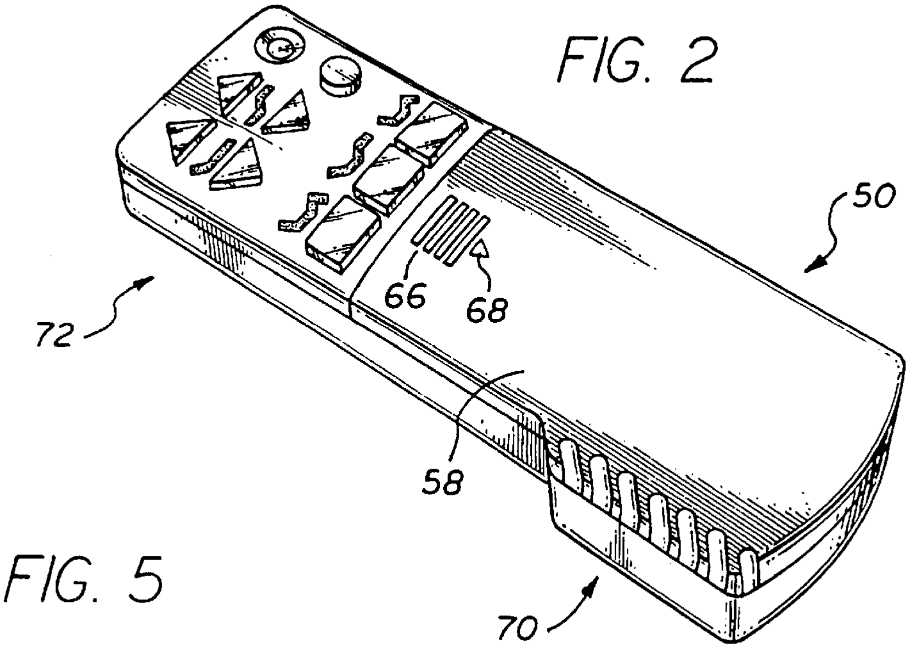
FIG. 2 is a perspective view of the simplified remote control unit of the articulated bed assembly.
Figure 5:
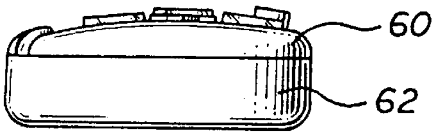
FIG. 5 is a bottom view of the simplified remote control unit.
Figure 3:
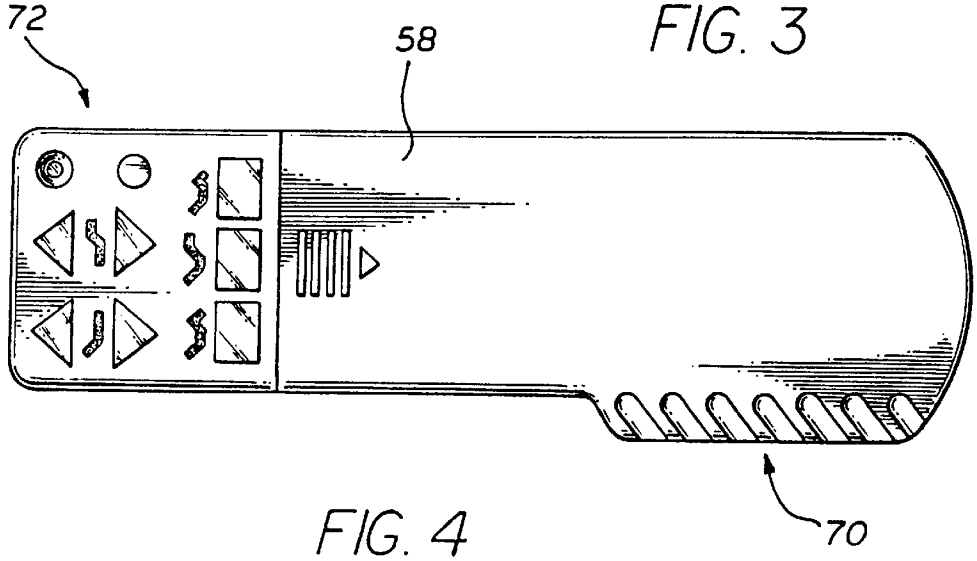
FIG. 3 is a front view of the simplified remote control unit.
Figure 4:
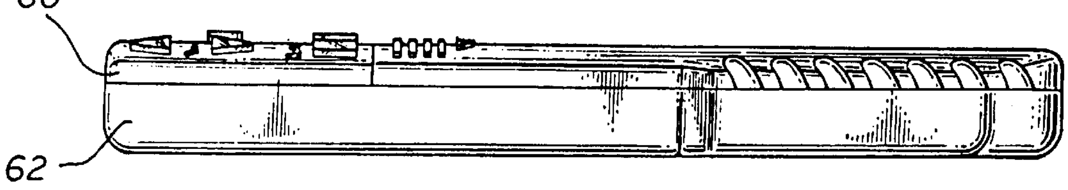
FIG. 4 is a left side view of the simplified remote control unit.

FIGS. 2 and 3 show a preferred embodiment of the remote control unit 50 which includes a housing 56 with a slidable face cover 58. The housing 56, which is preferably sized to be conveniently held in an adult's hand, and the face cover 58 may be formed from an inexpensive plastic such as polystyrene. As shown in FIGS. 4, 5, 6 and 8, the housing 56 is preferably separated into a top shell 60 and a matching bottom shell 62 which are fitted together defining an inner chamber. FIG. 7 shows that a screw 64 may be fitted through the bottom shell 62 and into the top shell 60 securing shells 60, 62 together. As may be readily appreciated, any of a number of conventional fastening means may be utilized to secure the top shell 60 to the bottom shell 62, for example, latches, screws, force fitting members, etc.

As is best illustrated in FIGS. 2 and 3, the face cover 58 advantageously includes a plurality of parallel ridges 66 which may be gripped by the user's thumb to slide the face cover 58 in the direction of an arrow 68 which appears on the face cover. Preferably, the shells 60, 62 and the face cover 58 are asymmetrically shaped along a length of the remote control unit 50 so that a user will become more familiar with the shape of the unit 50 and thus be able to more quickly orient the unit within his or her hand. For example, the remote control unit 50 may be formed with an extended portion 70 which quickly identifies which portion of the unit 50 is to be held in the user's hand, even when little or no light is available in the room.

An important feature of the present invention is the face cover 58 which conceals some of the user mechanisms to simplify operation of the remote control unit 50. The subject matter of the present invention additionally contemplates a face cover 58 which is secured to the housing 56 by a hinge or other mechanism. Generally the cover 58 provides a simple way of alternatively concealing and accessing some of the user mechanisms as desired.

To this end, the remote control unit 50 provides a limited selection of buttons when the face cover 58 is slid into its closed position. More specifically, and as is shown in FIGS. 2 and 3, only a first group of buttons 72 is accessible to the user when the face cover 58 is slid into its closed position. FIG. 9 shows the remote control unit 50 with the face cover 58 slid into its opened position. A second group of buttons 74 becomes accessible to the user when the face cover 58 is slid into the opened position.

Figure 10:
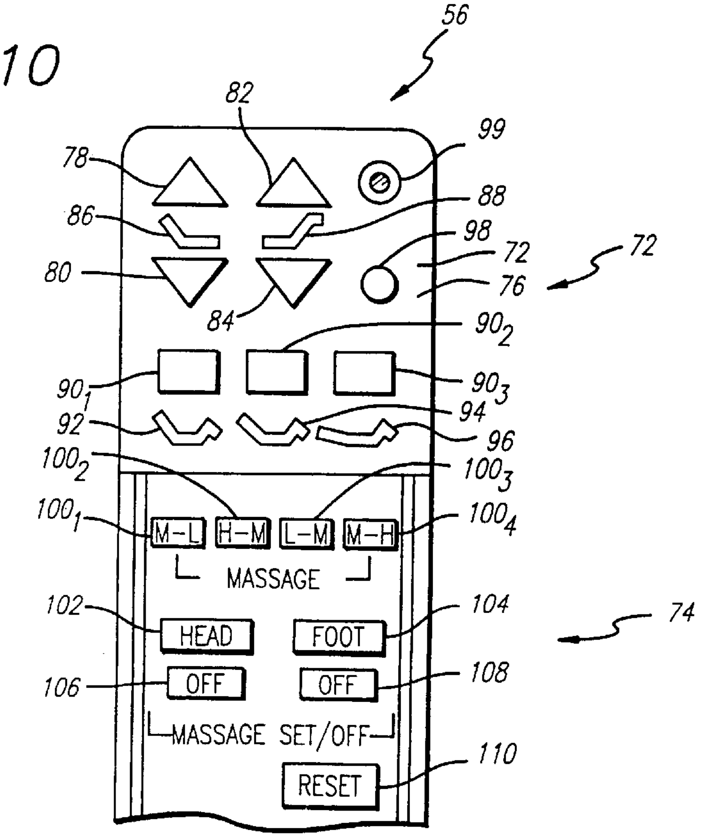
FIG. 10 is an enlarged front view of the simplified remote control unit with its slidable face cover in the open position.

FIG. 10 is an enlarged front view of the remote control unit 50 with the face cover 58 slid into its opened position. The first group of buttons 72 are fitted within the housing 56 and extend therefrom at a front portion 76 of the housing 56. An additional feature of the present invention is that the first group of buttons 72 is positioned within the front portion 76, shaped, and labeled with distinguishing icons depending upon the functions of the respective buttons within the first group 72. Accordingly, and as illustrated in FIG. 10, the front portion 76 also includes a plurality of icons adjacent to the first group of buttons 72. More specifically, the first group of buttons 72 includes a pair of head portion elevation buttons 78, 80 which respectively generate a raise head portion signal and a lower head portion signal when pressed by the user. The first group of buttons 72 also include a pair of foot portion elevation buttons 82, 84 which respectively provide a raise foot portion signal and a lower foot portion signal when pressed by user. A head portion elevation icon 86 may be positioned on the front portion 76 between the elevation buttons 78, 80. Similarly, a foot portion elevation icon 88 may be positioned on the front portion 76 between the elevation buttons 82, 84. Icons 86, 88 and all hereinafter described icons are preferably applied to the front portion 76 in the form of a visible (or even fluorescent) ink, dye, decal, paint, label, etc. The head portion elevation icon 86 is preferably a simplified profile of the bed assembly 20 shown with the head portion 40 in a raised position. The foot portion elevation icon 88 is preferably a simplified profile of the bed assembly 20 shown with the thigh portion 44 and the foot portion 46 in a raised position.

Elevation buttons 78, 80, 82, 84 are preferably shaped as equilateral triangles and the buttons are preferably oriented such that the base side of the buttons triangular shape faces its corresponding icon. The elevation buttons 78, 80, 82, 84 are all triangularly shaped and oriented to either point in an upward or downward direction along the length of the remote control unit 50. Since each pair of elevation buttons is clearly and visibly associated with an icon, the function of each of the buttons is abundantly clear even to a user who is inexperienced with or intimidated by remote control devices. Thus, the elevation buttons 78, 80, 82, 84 are preferably of a first shape such as the above-described equilateral triangle. Furthermore, the buttons included within the first group 72 may be formed in distinctly different geometric shapes depending upon their function.

The first group of buttons 72 also includes a plurality of preset bed position buttons $\mathbf{90}_1$, $\mathbf{90}_2$, $\mathbf{90}_3$ which are preferably arranged in a horizontal row perpendicular to the length of the remote control unit 50. The preset bed position buttons $\mathbf{90}_1$, $\mathbf{90}_2$, $\mathbf{90}_3$ are formed in a second shape which is preferably, but not necessarily, that of a rectangle. Corresponding preset bed position icons 92, 94, 96 are respectively positioned on the front portion 76 adjacent to the present bed position buttons $\mathbf{90}_1$, $\mathbf{90}_2$, $\mathbf{90}_3$.

When any of the preset bed position buttons $\mathbf{90}_1$, $\mathbf{90}_2$, $\mathbf{90}_3$ are pressed by the user a bed position preset signal is generated and the bed controller unit 48 responds by appropriately driving the elevation motors 32, 34 to positions which respectively correspond to "chair", "lounge" and "back relief". For example, the foregoing preset bed positions may be defined in terms of the angle $\phi_h$ measured between the base 22 and the support plate $\mathbf{26}_1$ and the angle $\phi_f$ measured between the base 22 and the support plate $\mathbf{26}_3$ (FIG. 1). When button $\mathbf{90}_1$ is pressed, the controller unit 48 drives the bed assembly 20 into the preset "chair" position wherein $\phi_h$=54° and $\phi_f$=13°. When button $\mathbf{90}_2$ is pressed, the bed assembly 20 is similarly manipulated into the "lounge" position such that $\phi 1_h$=37° and $\phi_f$=19°. When button $\mathbf{90}_3$ is pressed, the bed assembly 20 is driven by the motors 32, 34 into the "back relief" position wherein $\phi_h$=5° and $\phi_f$=40°. As may be readily appreciated, the aforedescribed preset positions are merely exemplary and are not intended to serve a limiting purpose insofar as how the bed control unit 48 may be programmed to drive the elevation motors 32, 34 to position the mattress 30 in various preset bed positions.

In operation, a user presses one of the preset bed position buttons $\mathbf{90}_1$, $\mathbf{90}_2$, $\mathbf{90}_3$ to manipulate the bed assembly 20 as desired. The preset bed position icons 92, 94, 96 are preferably simplified profiles of the bed assembly 20 shaped as the desired preset position. Accordingly, the icon 92 should closely resemble the "chair" preset position described above. The preset bed position icons 92, 94 should likewise resemble the bed assembly 20 after it has been manipulated into the above-described "lounge" and "back relief" preset positions respectively.

Although the above-described preset bed positions have been ergonomically selected to accommodate the needs of a great many users, the bed controller unit 48 is preferably designed to permit a-finer adjustment of the positions of the head portion 40 or the thigh portion 44 and foot portion 46 after the preset bed position has been reached by pressing the elevation buttons 78, 80, 82, 84. Additionally, the bed controller unit 48 may be programmed (or include logic circuitry) to stop all movements of the head portion 40, the thigh portion 44, and the foot portion 46 when any of the buttons on the remote control unit 50 is pressed while the bed controller unit 48 is controlling the movement of bed assembly 20 to any of the preset bed positions. Such a safety feature is clearly desirable in that a user of the remote control unit 50 need not frantically search for a particular button which alone is capable of stopping the bed's movement should, for example, a limb, small child, or pet inadvertently position itself between the base and the articulated support plate $\mathbf{26}_1$, $\mathbf{26}_3$, $\mathbf{26}_4$.

The first group of buttons 72 also includes a stored massage button 98 which provides a stored massage signal. The stored massage button 98 is of a third shape which is preferably, but not necessarily, circular. In keeping with the spirit of simplification, the bed controller unit 48 controls the massage motors 52, 54 according to a stored massage mode which may, for example, be the last massage selected. Lastly, the first group of buttons 72 may also include a light emitting device 99 such as a light emitting diode (LED) for indicating when the remote control unit 50 is operating, when a battery therein is generating insufficient current, etc.

At this point, it is worthwhile to note that all of the buttons may be more broadly described as user activated mechanisms. As such, the contemplated subject matter of the present invention additionally includes user activated mechanisms such as switches, levers, heat and Light sensing elements, etc. Although the preferred buttons are raised relative to the housing 56, such a tactile construction is not an indispensable element of the simplified remote control unit 50.

The second group of buttons 74 is positioned on the housing 56 and concealable by the face cover 58. Accordingly, a nurse or other more capable user of the remote control unit 50 may access and thereby utilize additional capabilities of the bed controller unit 48 via the remote control unit 50. The second group of buttons 74 includes a plurality of preset massage buttons $\mathbf{100}_1$, $\mathbf{100}_2$, $\mathbf{100}_3$, $\mathbf{100}_4$. The preferred bed controller unit 48 is designed to drive the head massage motor 52 at predetermined low, medium and high head massage motor frequencies. Similarly, the controller unit 48 drives the foot massage motor 54 at predetermined low, medium and high foot massage motor frequencies. It has been observed that the articulated bed assembly 20 provides a different quality massage depending upon how much the bed assembly 20 is loaded (i.e., the user's weight). For example, a person who weighs one hundred and ten pounds may prefer a massage wherein the head massage motor 52 operates at its predetermined medium head massage motor frequency and wherein the foot massage motor 54 operates at its predetermined low foot massage motor frequency. Such a massage is commanded by the bed controller unit 48 when the button $\mathbf{100}_1$ is pressed by the user.

As shown in FIG. 10, the legend "M-L" is inscribed upon, marked on, or otherwise applied to the preset massage button $\mathbf{100}_1$. By way of further example, a person who weighs over 200 lbs. may prefer the massage which results from pressing the button $\mathbf{100}_2$ wherein the head massage motor 52 operates at its predetermined high frequency and wherein the foot massage motor 54 operates at its predetermined medium frequency. The massage modes corresponding to buttons $\mathbf{100}_3$, $\mathbf{100}_4$ respectively correspond to "L-M" and "M-H" massage modes and are not further described.

The bed controller unit 48 is designed to begin a user selected massage mode upon the user's activation of any of the preset massage buttons 100$_1$, 100$_2$, 100$_3$, 100$_4$. Such a massage will continue for a predetermined period of time, such as five minutes, and then automatically terminate. Selection of any of the preset massage buttons 100$_1$, 100$_2$, 100$_3$, 100$_4$ generates a massage motors preset signal which is provided to the controller unit 48. In response, the controller unit 48 generates the head and foot massage signals which respectively drive the massage motors 52, 54.

When any of the preset massage buttons 100$_1$, 100$_2$, 100$_3$, 100$_4$ are pressed, the head massage signal is provided to the head massage motor 52 as a head massage motor "on" signal at either the predetermined low, medium or high head massage motor frequency during the duration of the selected massage. Similarly, the foot massage signal is provided to the foot massage motor 54 as a foot massage motor "on" signal at the predetermined low, medium or high foot massage motor frequency depending upon which massage mode was selected. After the preselected massage terminates, the bed controller unit 48 provides the head massage signal as a head massage motor "off" signal and the foot massage signal as a foot massage motor "off" signal thus stopping all vibrations of the bed assembly 20.

The second group of buttons 74 additionally includes a head massage motor speed adjustment button 102 and a foot massage motor speed adjustment button 104. Both buttons 102, 104 override a preset massage. More specifically, the head massage motor speed adjustment button 102 sequentially cycles the head massage motor "on" signal through the predetermined low, medium and high head massage motor frequencies. Similarly, the foot massage motor speed adjustment button 104 sequentially cycles the foot massage motor "on" signal through the predetermined low, medium and high foot massage motor frequencies. Thus, and by way of example, a person who has pressed preset massage button 100$_1$ may increase the intensity of the massage felt at the foot portion 46 by pressing the button 104 one time. Preferably, buttons 102, 104 are respectively labeled "HEAD" and "FOOT".

The second group of buttons 74 also includes a head massage motor stop button 106 and a foot massage motor stop button 108. The buttons 106, 108 both override any massage mode presently being controlled by the controller unit 48. More specifically, the head massage motor stop button 106 causes the controller unit 48 to provide the head massage signal as the head massage motor "off" signal. Likewise, when the user presses the foot massage motor stop button 108, the controller unit 48 provides the foot massage signal as the foot massage motor "off" signal. Additionally, the second group of buttons 74 includes a reset button 110 which causes all massage motors to stop and returns the bed assembly 20 to a level position. Hence, a more capable user may initiate one of the four preferred massage modes, adjust the speed of the massage motors 52, 54, or stop the massage as desired by simply sliding back the face cover 58 to access the second group of buttons 74. A more detailed description of the controller unit 48 and the remote control unit 50 follows.

Figure 11:
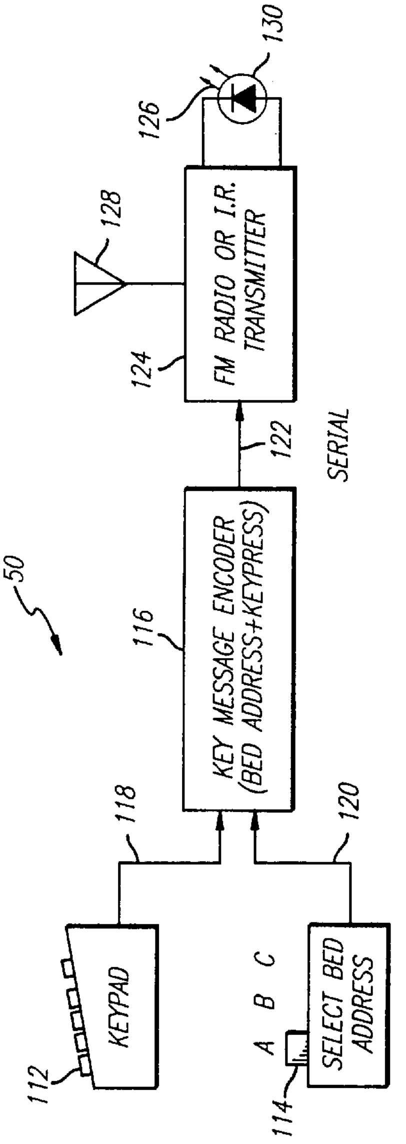
FIG. 11 is a functional block diagram of the simplified remote control unit.

FIG. 11 shows a functional block diagram of the simplified remote control unit 50. The plurality of buttons are fitted within the housing 56 in the form of a key pad 112. A bed address selector switch 114 and the key pad 112 both provide outputs to an encoder 116. The key pad 112 outputs user input signals 118 from both the first and second groups of buttons 72, 74. The user input signals 118 generated by the first group of buttons 72 include the raise head portion signal, the lower head portion signal, the raise foot portion signal, the lower foot portion signal, the bed position preset signal, and the stored massage signal. The user input signals generated by the second group of buttons 74 include the head massage motor speed signal, the foot massage motor speed signal, and the massage motor's preset signal. The output 120 of the bed address switch 114 and the user input signals 118 are received by the encoder 116 which generates an encoded signal 122. The remote control unit 50 additionally includes a transmitter 124 which receives the encoded signal 122 and transmits a modulated encoded signal 126. The transmitter 124 may include a conventional FM radio transmitter with antenna 128 or a conventional infrared emitting device 130.

The bed address information provided at output 120 allows more than one articulated bed assembly 20 to be used within close proximity. The bed controller unit 48 preferably includes a corresponding bed address switch, To this end, the preferred encoder 116 is a C-MOS Motorola MC145026 encoder chip of Motorola's commonly utilized MC145026/27 encoder/decoder pair. Accordingly, the bed controller unit 48 which receives and decodes the user input signals 118, as provided to it by the remote control unit 50, preferably includes a Motorola MC145027 decoder chip. As may be readily appreciated, other encoder/decoder pairs or functionally equivalent circuitry may be employed in lieu of the preferred encoder/decoder pair.

Figure 12:
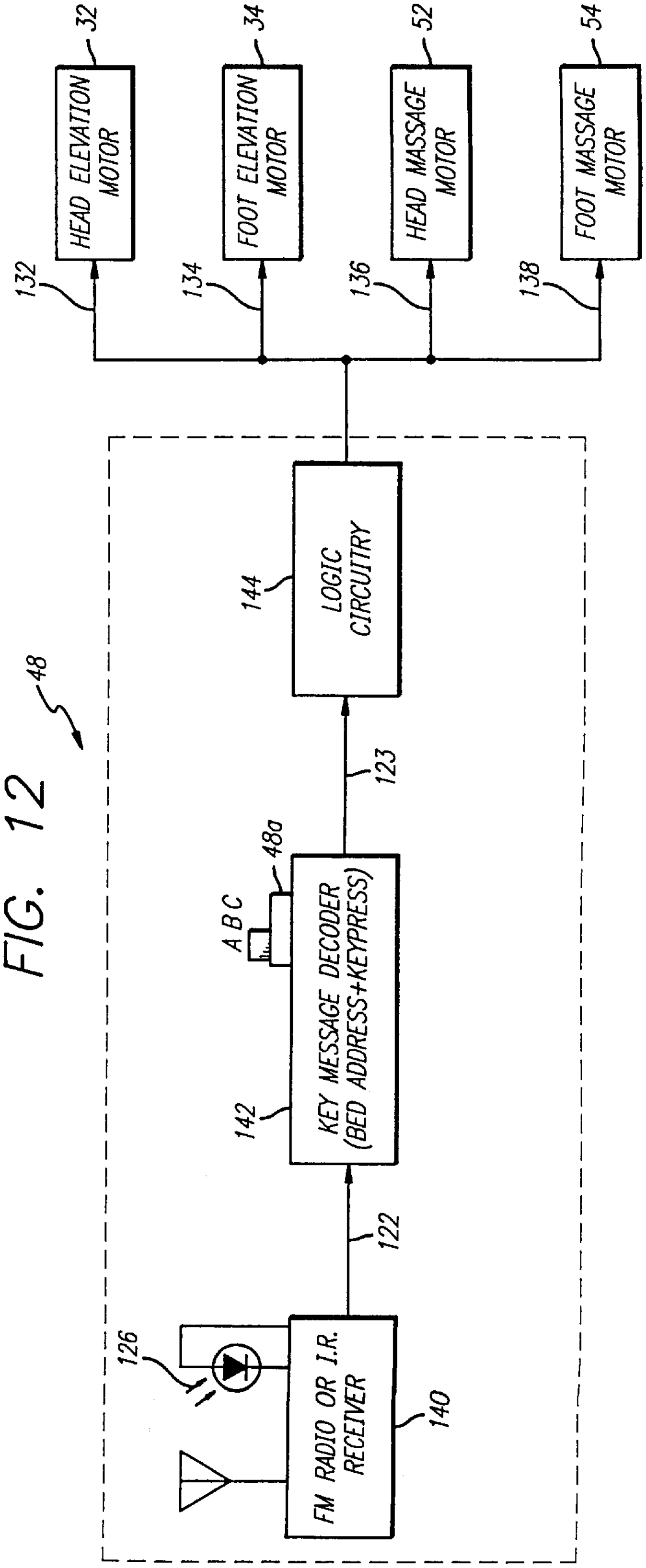
FIG. 12 is a functional block diagram of the bed controller unit.
Figure 13:
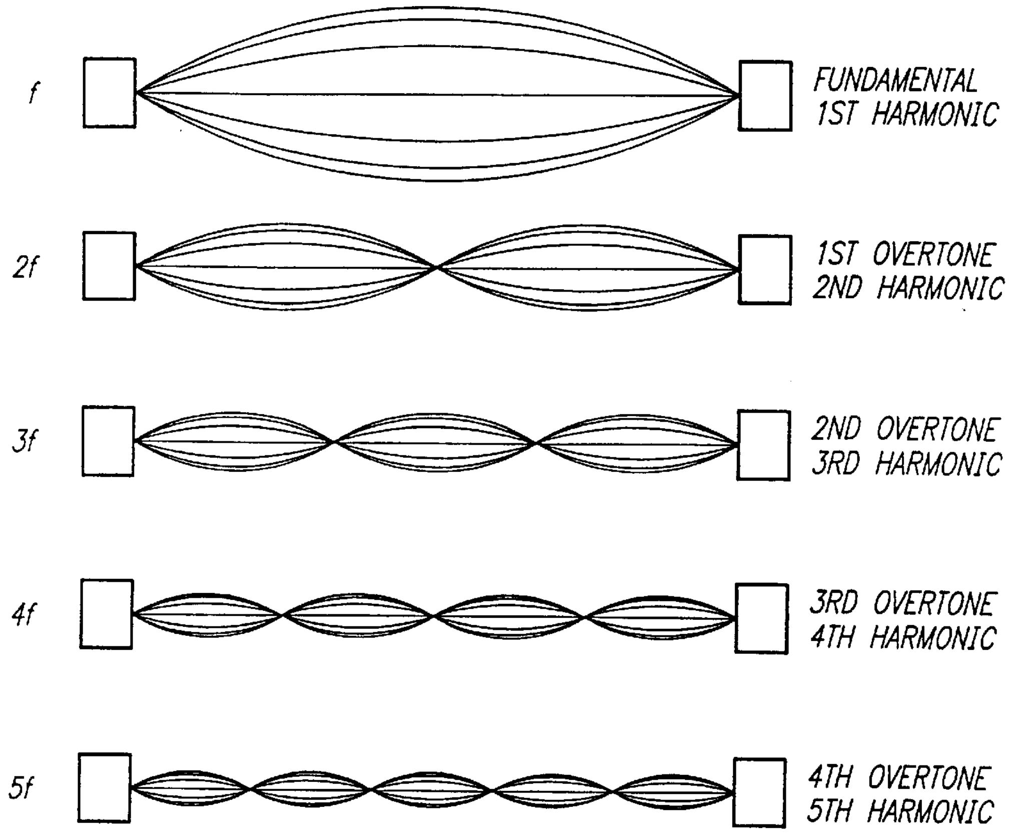
FIG. 13 shows a fundamental frequency of the head or foot massage motor and harmonics thereof.

FIG. 12 shows a simplified block diagram of the bed controller unit 48. Additionally, FIG. 12 shows that the controller unit 48 provides the head elevation motor 32 with the head elevation signal 132, the foot elevation motor 34 with the foot elevation signal 134, the head massage motor 52 with the head massage signal 136, and the foot massage motor 54 with the foot massage signal 138. In the illustrated embodiment, the bed controller unit 48 includes a receiver 140, a decoder 142 and logic circuitry 144. The receiver 140 receives and demodulates the modulated encoded signal 126 from the remote control unit 50 to provide the encoded signal 122 to the decoder 142. The decoder 142 additionally receives a bed address switch input as discussed above, and, accordingly, only decodes user input signals which are sent by the remote control unit 50 whose address matches that of the control unit 48. The decoder 142 provides decoded user input signals 123 to the logic circuitry 144 which, in turn, generates the head elevation signal 132, the foot elevation signal 134, the head massage signal 136, and the foot massage signal 138. The logic circuitry 144 may alternatively be realized in the form of a processor and/or may include timers for determining the duration of the above-described preset massages.

Figure 14:
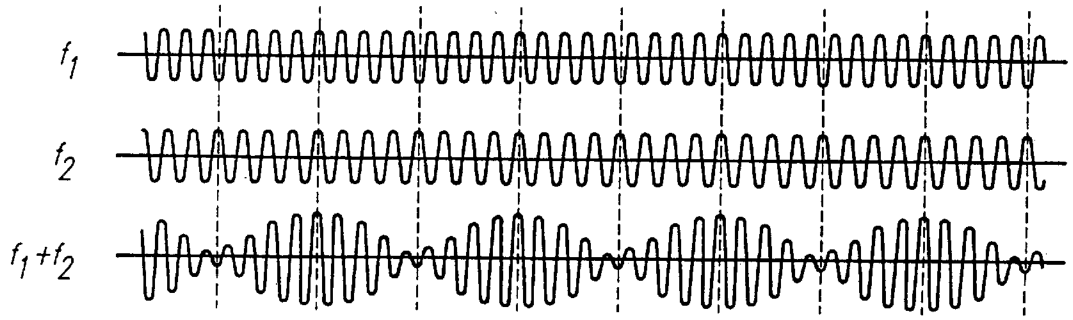
FIG. 14 shows how a fundamental frequency of either the head or foot massage motor may combine with harmonics of the other massage motor to generate a beat frequency vibration effect between the head and foot portions of the bed.

A further aspect of the present invention is conceptually illustrated in FIGS. 14 and 15, the former illustrating that a member vibrating at a fundamental frequency exhibits vibratory harmonic components. It has been observed that the predetermined low, medium and high head massage motor frequencies and the predetermined low, medium and high foot massage motor frequencies may be controlled by the logic circuitry 144 such that the controller unit 48 provides a beat frequency vibration effect between the head portion 40 and the foot portion 46 of the bed assembly 20. By appropriately selecting the aforementioned frequencies, a harmonic of the head massage motor 52 is close enough to the fundamental frequency of the foot massage motor 54 (or vice versa) thereby providing a beat frequency vibration effect noticeable to the user. For example, FIG. 15 shows a first frequency $f_1$ corresponding to a harmonic of the head massage motor 52 and a second frequency $f_2$ corresponding to the fundamental frequency of the foot massage motor 54. The additive effect of $f_1$ and $f_2$ which are close in frequency results in the beat frequency vibration effect shown in the plot designated as $f_1+f_2$.

Those skilled in the art will appreciate that various adaptations and modifications of the just described preferred embodiment can be configured without departing from the scope and spirit of the invention. Therefore, it is to be understood that, within the scope of the appended claims, the invention may be practiced other than as specifically described herein. For example, the simplified remote control unit may be readily modified for the purpose of controlling a television, a compact disk player, or the like.

I claim:

1. An adjustable massage bed assembly, comprising:

a head motor for controllably raising and lowering a head section of a mattress;

a foot motor for controllably raising and lowering a foot section of the mattress;

a vibratory motor for imparting a massaging action to a portion of the mattress;

and a handheld control unit including first and second mechanisms for controlling operations of said head and foot motors, and a third mechanism for controlling an operation of said vibratory motor;

wherein said third mechanism when actuated also stops any operation of said head and foot motors as a safety feature.

2. The bed assembly of claim 1 wherein said vibratory motor defines a head vibratory motor and said mattress portion defines a mattress head portion, and further comprising a foot vibratory motor for imparting a massaging action to a foot portion of the mattress, and said control unit includes a fourth mechanism for controlling an operation of said foot vibratory motor, wherein said fourth mechanism when actuated also stops any operation of said head and foot motors as a safety feature.

3. The bed assembly of claim 2 wherein said first, second, third and fourth mechanisms comprise respectively first, second, third and fourth depressible buttons.

4. The bed assembly of claim 1 wherein said control unit is a wireless remote handheld control unit.

5. The bed assembly of claim 1 wherein said first mechanism controls operation of said head motor but not said foot motor and said second mechanism controls operation of said foot motor but not said head motor.

6. The bed assembly of claim 1 wherein said first mechanism operates both said head and foot motors to cause the mattress to assume a first predetermined mattress head-foot configuration, and said second mechanism operates both said head and foot motors to cause the mattress to assume a different second predetermined mattress head-foot configuration.

7. The bed assembly of claim 1 wherein said control unit includes first and second groups of control buttons and a slidable cover which slides between an open position operatively exposing both said first and second groups and a cover position operatively covering said second group and operatively exposing said first group.

8. The bed assembly of claim 1 wherein said control unit includes a fourth mechanism which when actuated causes said vibratory motor to sequentially cycle through predetermined low, medium and high motor frequencies.

9. The bed assembly of claim 1 further comprising said vibratory motor defining a first vibratory motor, said mattress portion defining a mattress first portion, a second vibratory motor for imparting a massaging action to a mattress second portion, said control unit including a stored massage mechanism which when actuated causes said first vibratory motor to automatically vibrate at a first predetermined frequency and said second vibratory motor to automatically vibrate at a second predetermined frequency.

10. The bed assembly of claim 8 wherein said fourth mechanism when actuated stops any ongoing operation of said head and foot motors as a safety feature of said bed assembly.

11. The bed assembly of claim 1 wherein said handheld control unit includes a preset position mechanism which when actuated causes at least one of said head and foot motors to operate and move at least one of the head and foot sections to respective predetermined positions, both angled relative to a horizontal.

12. The bed assembly of claim 11 wherein said preset position mechanism when actuated stops any ongoing operation of said head and foot motors as a safety feature of said bed assembly.

13. The bed assembly of claim 1 wherein said first, second and third mechanisms comprise depressible buttons on a face of said handheld control unit.

14. The bed assembly of claim 7 wherein said slidable cover is manually slidable longitudinally relative to said control unit by a user between the open and cover positions.

* * * * *